(12) United States Patent
Dageville et al.

(10) Patent No.: US 9,842,152 B2
(45) Date of Patent: Dec. 12, 2017

(54) TRANSPARENT DISCOVERY OF SEMI-STRUCTURED DATA SCHEMA

(71) Applicant: Snowflake Computing Inc., San Mateo, CA (US)

(72) Inventors: Benoit Dageville, Foster City, CA (US); Vadim Antonov, Belmont, CA (US)

(73) Assignee: Snowflake Computing, Inc., San Mateo, CA (US)

( * ) Notice: Subject to any disclaimer, the term of this patent is extended or adjusted under 35 U.S.C. 154(b) by 457 days.

(21) Appl. No.: 14/518,931

(22) Filed: Oct. 20, 2014

(65) Prior Publication Data

US 2015/0234931 A1 Aug. 20, 2015

Related U.S. Application Data

(60) Provisional application No. 61/941,986, filed on Feb. 19, 2014.

(51) Int. Cl.
*G06F 17/30* (2006.01)
*G06F 9/50* (2006.01)
*G06F 9/48* (2006.01)
*H04L 29/08* (2006.01)

(52) U.S. Cl.
CPC ...... *G06F 17/30575* (2013.01); *G06F 9/4881* (2013.01); *G06F 9/5016* (2013.01); *G06F 9/5088* (2013.01); *G06F 17/302* (2013.01); *G06F 17/3048* (2013.01); *G06F 17/30292* (2013.01); *G06F 17/30315* (2013.01); *G06F 17/30371* (2013.01); *G06F 17/30463* (2013.01); *G06F 17/30466* (2013.01); *G06F 17/30498* (2013.01); *G06F 17/30545* (2013.01); *G06F 17/30598* (2013.01); *G06F 17/30864* (2013.01); *G06F 17/30867* (2013.01); *G06F 17/30914* (2013.01); *H04L 67/1095* (2013.01); *H04L 67/2842* (2013.01)

(58) Field of Classification Search
CPC ............. G06F 17/30575; G06F 9/4881; G06F 9/5016; G06F 9/5088; G06F 17/302; G06F 17/30292; G06F 17/30315; G06F 17/30371; G06F 17/30463; G06F 17/30466; G06F 17/3048; G06F 17/30498; G06F 17/30545; G06F 17/30598; G06F 17/30864; G06F 17/30867; G06F 17/30914; H04L 67/1095; H04L 67/2842

See application file for complete search history.

(56) References Cited

U.S. PATENT DOCUMENTS 5,787,466 A 7/1998 Berliner
6,338,056 B1 * 1/2002 Dessloch .......... G06F 17/30321
707/711
6,490,590 B1 12/2002 Fink
(Continued)

FOREIGN PATENT DOCUMENTS

CN 102496060 6/2012
CN 203261358 10/2013
(Continued)

*Primary Examiner* — Noosha Arjomandi
(74) *Attorney, Agent, or Firm* — David R. Stevens; Stevens Law Group

(57) ABSTRACT

A system, apparatus, and method for managing data storage and data access for semi-structured data systems.

18 Claims, 6 Drawing Sheets

(56) References Cited

U.S. PATENT DOCUMENTS

| | | | |
|---|---|---|---|
| 6,604,100 B1* | 8/2003 | Fernandez | G06F 17/2247 |
| 6,757,689 B2 | 6/2004 | Battas | |
| 7,280,998 B1 | 10/2007 | Aboujaoude | |
| 7,823,009 B1 | 10/2010 | Tormasov | |
| 8,341,363 B2 | 12/2012 | Chou | |
| 8,381,015 B2 | 2/2013 | Kaminski | |
| 8,428,087 B1 | 4/2013 | Vincent | |
| 8,516,159 B2 | 8/2013 | Ananthanarayanan | |
| 8,516,355 B2 | 8/2013 | Gale | |
| 8,560,887 B2 | 10/2013 | Behrendt | |
| 8,640,137 B1 | 1/2014 | Bostic et al. | |
| 8,706,914 B2 | 4/2014 | Duchesneau | |
| 8,725,875 B2 | 5/2014 | Supalov | |
| 8,849,764 B1* | 9/2014 | Long | G06F 11/1451 |
| | | | 707/646 |
| 9,229,967 B2* | 1/2016 | Ge | |
| 2002/0120598 A1* | 8/2002 | Shadmon | G06F 17/30911 |
| 2002/0120630 A1 | 8/2002 | Christianson et al. | |
| 2003/0158884 A1 | 8/2003 | Alford, Jr. | |
| 2003/0177239 A1 | 9/2003 | Shinohara et al. | |
| 2004/0167904 A1* | 8/2004 | Wen | G06F 17/30914 |
| 2005/0050054 A1* | 3/2005 | Clark | G06F 17/30174 |
| 2005/0210049 A1 | 9/2005 | Foster | |
| 2005/0223047 A1* | 10/2005 | Shah | G06F 17/30575 |
| 2006/0059173 A1 | 3/2006 | Hirsch et al. | |
| 2006/0074872 A1 | 4/2006 | Gordon | |
| 2007/0112714 A1* | 5/2007 | Fairweather | G06F 8/427 |
| | | | 706/46 |
| 2007/0198656 A1 | 8/2007 | Mazzaferri et al. | |
| 2007/0276861 A1 | 11/2007 | Pryce et al. | |
| 2008/0027788 A1 | 1/2008 | Lawrence et al. | |
| 2008/0027965 A1 | 1/2008 | Garrett et al. | |
| 2009/0182836 A1 | 7/2009 | Aviles et al. | |
| 2009/0234711 A1* | 9/2009 | Ramer | G06F 17/30749 |
| | | | 705/14.66 |
| 2009/0254516 A1 | 10/2009 | Meiyyappan et al. | |
| 2009/0254532 A1 | 10/2009 | Yang et al. | |
| 2009/0300043 A1 | 12/2009 | Maclennan | |
| 2010/0005054 A1* | 1/2010 | Smith | G06F 17/30498 |
| | | | 707/E17.002 |
| 2010/0031267 A1 | 2/2010 | Maessen et al. | |
| 2010/0100888 A1 | 4/2010 | Tene et al. | |
| 2010/0145929 A1 | 6/2010 | Burger | |
| 2010/0179940 A1 | 7/2010 | Gilder et al. | |
| 2010/0199042 A1 | 8/2010 | Bates | |
| 2011/0145307 A1 | 6/2011 | Ananthanarayanan et al. | |
| 2011/0145489 A1* | 6/2011 | Yu | G06F 3/0613 |
| | | | 711/103 |
| 2011/0161488 A1 | 6/2011 | Anderson et al. | |
| 2011/0225167 A1* | 9/2011 | Bhattacharjee | G06F 17/30595 |
| | | | 707/747 |
| 2011/0314001 A1* | 12/2011 | Jacobs | G06F 17/30672 |
| | | | 707/722 |
| 2012/0005307 A1 | 1/2012 | Das et al. | |
| 2012/0101860 A1 | 4/2012 | Ezzat | |
| 2012/0109888 A1 | 5/2012 | Zhang et al. | |
| 2012/0110570 A1 | 5/2012 | Jacobson | |
| 2012/0166771 A1 | 6/2012 | Ringseth | |
| 2012/0173824 A1 | 7/2012 | Iyigun et al. | |
| 2012/0204187 A1 | 8/2012 | Breiter et al. | |
| 2012/0233315 A1 | 9/2012 | Hoffman | |
| 2012/0260050 A1 | 10/2012 | Kaliannan | |
| 2012/0265881 A1 | 10/2012 | Chen | |
| 2012/0296883 A1 | 11/2012 | Ganesh et al. | |
| 2012/0311065 A1 | 12/2012 | Ananthanarayanan et al. | |
| 2012/0323971 A1 | 12/2012 | Pasupuleti | |
| 2013/0007753 A1 | 1/2013 | Jain | |
| 2013/0110778 A1 | 5/2013 | Taylor et al. | |
| 2013/0110961 A1 | 5/2013 | Jadhav | |
| 2013/0124545 A1 | 5/2013 | Holmberg et al. | |
| 2013/0132967 A1 | 5/2013 | Soundararajan | |
| 2013/0145375 A1 | 6/2013 | Kang | |
| 2013/0151884 A1 | 6/2013 | Hsu | |
| 2013/0174146 A1 | 7/2013 | Dasgupta | |
| 2013/0205028 A1 | 8/2013 | Crockett et al. | |
| 2013/0205092 A1 | 8/2013 | Roy et al. | |
| 2013/0218837 A1 | 8/2013 | Bhatnagar | |
| 2013/0262386 A1* | 10/2013 | Kottomtharayil | G06F 17/30174 |
| | | | 707/635 |
| 2013/0282795 A1 | 10/2013 | Tsao | |
| 2013/0311454 A1* | 11/2013 | Ezzat | G06F 17/30539 |
| | | | 707/722 |
| 2013/0332614 A1 | 12/2013 | Brunk | |
| 2014/0025638 A1 | 1/2014 | Hu | |
| 2014/0059017 A1* | 2/2014 | Chaney | G06F 17/30595 |
| | | | 707/692 |
| 2014/0059226 A1 | 2/2014 | Messerli | |
| 2014/0095646 A1 | 4/2014 | Chan | |
| 2014/0109095 A1 | 4/2014 | Farkash | |
| 2014/0115091 A1 | 4/2014 | Lee | |
| 2014/0136473 A1 | 5/2014 | Faerber | |
| 2014/0149461 A1 | 5/2014 | Wijayaratne | |
| 2014/0189432 A1* | 7/2014 | Gokhale | G06F 17/30289 |
| | | | 714/41 |
| 2014/0189680 A1* | 7/2014 | Kripalani | G06F 11/3664 |
| | | | 717/176 |
| 2014/0236890 A1* | 8/2014 | Vasan | H04L 67/1097 |
| | | | 707/610 |
| 2014/0372384 A1* | 12/2014 | Long | G06F 17/30289 |
| | | | 707/679 |
| 2014/0379775 A1* | 12/2014 | Korangy | H04L 67/1002 |
| | | | 709/201 |
| 2015/0012551 A1* | 1/2015 | Dong | H04W 4/005 |
| | | | 707/755 |
| 2015/0234869 A1* | 8/2015 | Chan | G06F 17/30312 |
| | | | 707/603 |
| 2017/0177308 A1* | 6/2017 | Montagnon | G06N 5/02 |

FOREIGN PATENT DOCUMENTS

| | | |
|---|---|---|
| WO | WO 2006-026659 | 3/2006 |
| WO | WO 2013-006157 | 1/2013 |
| WO | WO2013072232 | 5/2013 |
| WO | WO2013084078 | 6/2013 |

* cited by examiner

TRANSPARENT DISCOVERY OF SEMI-STRUCTURED DATA SCHEMA

CROSS REFERENCE TO RELATED APPLICATIONS

This application claims the benefit of U.S. Provisional Application Ser. No. 61/941,986, entitled "Apparatus and method for enterprise data warehouse data processing on cloud infrastructure," filed Feb. 19, 2014, the disclosure of which is incorporated herein by reference in its entirety.

TECHNICAL FIELD

The present disclosure relates to resource management systems and methods that manage data storage and computing resources.

BACKGROUND

Many existing data storage and retrieval systems are available today. For example, in a shared-disk system, all data is stored on a shared storage device that is accessible from all of the processing nodes in a data cluster. In this type of system, all data changes are written to the shared storage device to ensure that all processing nodes in the data cluster access a consistent version of the data. As the number of processing nodes increases in a shared-disk system, the shared storage device (and the communication links between the processing nodes and the shared storage device) becomes a bottleneck that slows data read and data write operations. This bottleneck is further aggravated with the addition of more processing nodes. Thus, existing shared-disk systems have limited scalability due to this bottleneck problem.

Another existing data storage and retrieval system is referred to as a "shared-nothing architecture." In this architecture, data is distributed across multiple processing nodes such that each node stores a subset of the data in the entire database. When a new processing node is added or removed, the shared-nothing architecture must rearrange data across the multiple processing nodes. This rearrangement of data can be time-consuming and disruptive to data read and write operations executed during the data rearrangement. And, the affinity of data to a particular node can create "hot spots" on the data cluster for popular data. Further, since each processing node performs also the storage function, this architecture requires at least one processing node to store data. Thus, the shared-nothing architecture fails to store data if all processing nodes are removed. Additionally, management of data in a shared-nothing architecture is complex due to the distribution of data across many different processing nodes.

The systems and methods described herein provide an improved approach to data storage and data retrieval that alleviates the above-identified limitations of existing systems.

BRIEF DESCRIPTION OF THE DRAWINGS

Non-limiting and non-exhaustive embodiments of the present disclosure are described with reference to the following figures, wherein like reference numerals refer to like parts throughout the various figures unless otherwise specified.

DETAILED DESCRIPTION

Figure 1:
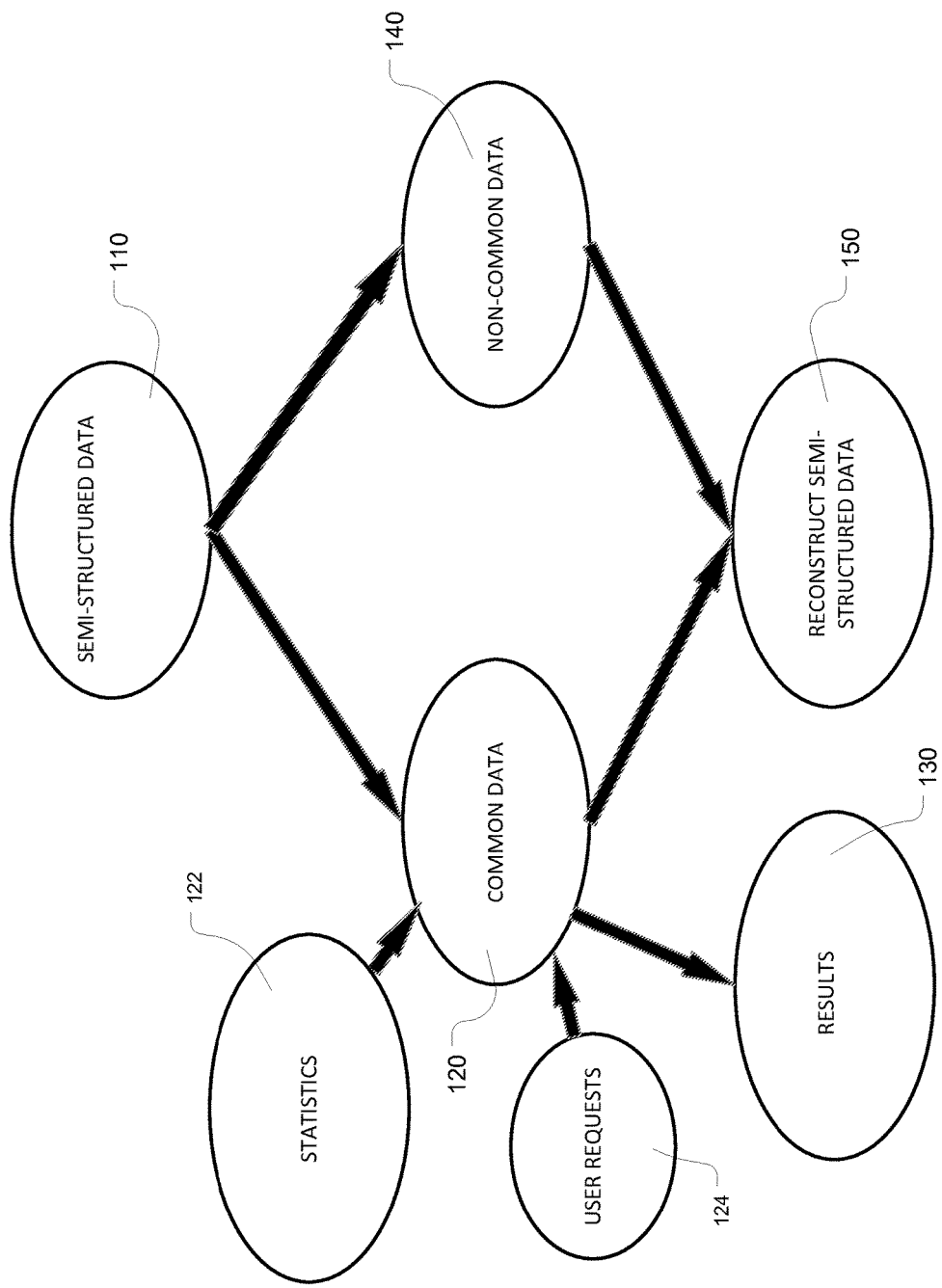
FIG. 1 illustrates an information flow and relatedness diagram depicting the processing of semi-structured data.

Disclosed herein are methods, apparatuses, and systems for managing semi-structured data. For example, an implementation of a method for managing semi-structured data may receive semi-structured data elements from a data source, and may perform statistical analysis on collections of the semi-structured data elements as they are added to the database. Additionally, common data elements from within the semi-structured data may be identified and may further combine the common data elements from the data source into separate pseudo-columns stored in cache memory. The implementation may further make metadata and statistics corresponding to the pseudo-columns available to a computer based query generator, and may store non-common data elements in an overflow serialized column in computer memory.

In the following description, reference is made to the accompanying drawings that form a part thereof, and in which is shown by way of illustration specific exemplary embodiments in which the disclosure may be practiced. These embodiments are described in sufficient detail to enable those skilled in the art to practice the concepts disclosed herein, and it is to be understood that modifications to the various disclosed embodiments may be made, and other embodiments may be utilized, without departing from the scope of the present disclosure. The following detailed description is, therefore, not to be taken in a limiting sense.

Reference throughout this specification to "one embodiment," "an embodiment," "one example" or "an example" means that a particular feature, structure or characteristic described in connection with the embodiment or example is included in at least one embodiment of the present disclosure. Thus, appearances of the phrases "in one embodiment," "in an embodiment," "one example" or "an example" in various places throughout this specification are not necessarily all referring to the same embodiment or example. In addition, it should be appreciated that the figures provided herewith are for explanation purposes to persons ordinarily skilled in the art and that the drawings are not necessarily drawn to scale.

Embodiments in accordance with the present disclosure may be embodied as an apparatus, method or computer program product. Accordingly, the present disclosure may take the form of an entirely hardware-comprised embodiment, an entirely software-comprised embodiment (including firmware, resident software, micro-code, etc.) or an embodiment combining software and hardware aspects that may all generally be referred to herein as a "circuit," "module" or "system." Furthermore, embodiments of the present disclosure may take the form of a computer program product embodied in any tangible medium of expression having computer-usable program code embodied in the medium.

Any combination of one or more computer-usable or computer-readable media may be utilized. For example, a computer-readable medium may include one or more of a portable computer diskette, a hard disk, a random access memory (RAM) device, a read-only memory (ROM) device, an erasable programmable read-only memory (EPROM or Flash memory) device, a portable compact disc read-only memory (CDROM), an optical storage device, and a magnetic storage device. Computer program code for carrying out operations of the present disclosure may be written in any combination of one or more programming languages. Such code may be compiled from source code to computer-readable assembly language or machine code suitable for the device or computer on which the code will be executed.

Embodiments may also be implemented in cloud computing environments. In this description and the following claims, "cloud computing" may be defined as a model for enabling ubiquitous, convenient, on-demand network access to a shared pool of configurable computing resources (e.g., networks, servers, storage, applications, and services) that can be rapidly provisioned via virtualization and released with minimal management effort or service provider interaction and then scaled accordingly. A cloud model can be composed of various characteristics (e.g., on-demand self-service, broad network access, resource pooling, rapid elasticity, and measured service), service models (e.g., Software as a Service ("SaaS"), Platform as a Service ("PaaS"), and Infrastructure as a Service ("IaaS")), and deployment models (e.g., private cloud, community cloud, public cloud, and hybrid cloud).

The flow diagrams and block diagrams in the attached figures illustrate the architecture, functionality, and operation of possible implementations of systems, methods, and computer program products according to various embodiments of the present disclosure. In this regard, each block in the flow diagrams or block diagrams may represent a module, segment, or portion of code, which comprises one or more executable instructions for implementing the specified logical function(s). It will also be noted that each block of the block diagrams and/or flow diagrams, and combinations of blocks in the block diagrams and/or flow diagrams, may be implemented by special purpose hardware-based systems that perform the specified functions or acts, or combinations of special purpose hardware and computer instructions. These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flow diagram and/or block diagram block or blocks.

The systems and methods described herein provide a flexible and scalable data warehouse using a new data processing platform. In some embodiments, the described systems and methods leverage a cloud infrastructure that supports cloud-based storage resources, computing resources, and the like. Example cloud-based storage resources offer significant storage capacity available on-demand at a low cost. Further, these cloud-based storage resources may be fault-tolerant and highly scalable, which can be costly to achieve in private data storage systems. Example cloud-based computing resources are available on-demand and may be priced based on actual usage levels of the resources. Typically, the cloud infrastructure is dynamically deployed, reconfigured, and decommissioned in a rapid manner.

In the described systems and methods, a data storage system utilizes a semi-structured based relational database. However, these systems and methods are applicable to any type of database using any data storage architecture and using any language to store and retrieve data within the database. As used herein, semi-structured data is meant to convey a form of structured data that does not conform with the typical formal structure of data models associated with relational, but nonetheless contains tags or other markers to separate semantic elements and enforce hierarchies of records and fields within the data. The systems and methods described herein further provide a multi-tenant system that supports isolation of computing resources and data between different customers/clients and between different users within the same customer/client.

Disclosed herein are methods and systems that significantly improve performance of databases and data warehouse systems handling large amounts of semi-structured data. Existing database systems are either relational (i.e. SQL databases) or key-value stores.

Relational databases can perform efficient queries due to query data access pruning (excluding portions of the database from the search based on aggregated metadata about values stored in specific columns of the tables). This, however, requires rigid tabular format of the data, which cannot be used to represent semi-structured data.

On the other hand, the key-value stores are more flexible, but introduce severe performance penalties due to lack of pruning. There is a number of ways to add handling of semi-structured data to relational databases in existing products and research projects:

1. Serialized encoding—a semi-structured data record is stored in a column as a serialized representation. Every time a value of some field is used, it is extracted and converted to an elementary type. This method is flexible, but makes access to this data to be improved by pruning, because extraction from serialized representation is costly, and requires significantly more CPU time than working with normal relational data. The entire serialized data records have to be read from persistent storage and processed even only a tiny portion (such as a single element) of them is used in the query.

2. Conversion at ingest—the semi-structured data is converted into relational data at the ingest. This makes access to this data as fast as access to any other relational data, but requires rigid specification of data structure at the ingest, and corresponding database schema to be fully specified beforehand. This method makes handling data with changing structure very costly because of the need to change database schema. Data with structure changing from record to record is impossible to handle using this method. The conversion method has to be specified apriori, and any non-trivial change will require re-ingesting the original semi-structured data.

3. Relational-like representation of structured data equivalent to object-attribute-value triplet representation stored in a conventional relational database. This method is flexible, but effectively requires join operations for access to data sub-components, which depending on data can be very slow.

4. Non-traditional extensions to relational data model, allowing columns with different cardinality to be linked in a hierarchy reflecting structure of the source data. The query generation methods for such data representation are not well-understood (and so no effective query generation is possible with the present state of the art). This method also requires input data to conform to a rigid (though non-tabular) schema, and thus is not sufficiently flexible to handle arbitrary semi-structured data.

What is needed is a system and method for working with semi-structured data that is efficient, low cost, and responsive, because it will preserve the semantics of the semi-structured data while managing the data in at least pseudo columns that can be processed and queried like more traditional data structures.

In an implementation of the following disclosure, data may come in the form of files, elements of files, portions of files, and the like. A file may comprise a collection of documents and portion of data may comprise a file, a plurality of documents from a connection, and/or a portion of documents. Further in the implementation, metadata may be associated with files, portions of files, and portions of data.

As used herein, the terms "common data elements" are intended to mean data elements belonging to the same group and collection of logically similar elements.

FIG. 1 illustrates a schematic of semi-structured data flow in a computer system processing semi-structured data. As can be seen the figure, semi-structured data 110 may comprise common and non-common data elements therein. In order to extract common data from the semi-structured data, analytic statistics 122 may be run against the semi-structured data to determine common data elements. Additionally, it should be noted that user interest 124 in certain data elements may also be used to determine common data. As illustrated in the figure, common data may be stored in temporary columnar structures called pseudo columns 120. Data elements that are not determined to be common may be stored serially in "overflow" serialized data 140. Ultimately a user will receive results 130 faster and accurately from the common data pseudo columns 120.

In the implementation, if the data element requested is not in a pseudo-column 120, it may be extracted from the "overflow" serialized data 140, and if an entire semi-structured data record 150 is requested, it may be reconstructed from the extracted data elements in pseudo-columns 120 and the "overflow" data 140 and re-serialized.

Figure 2:
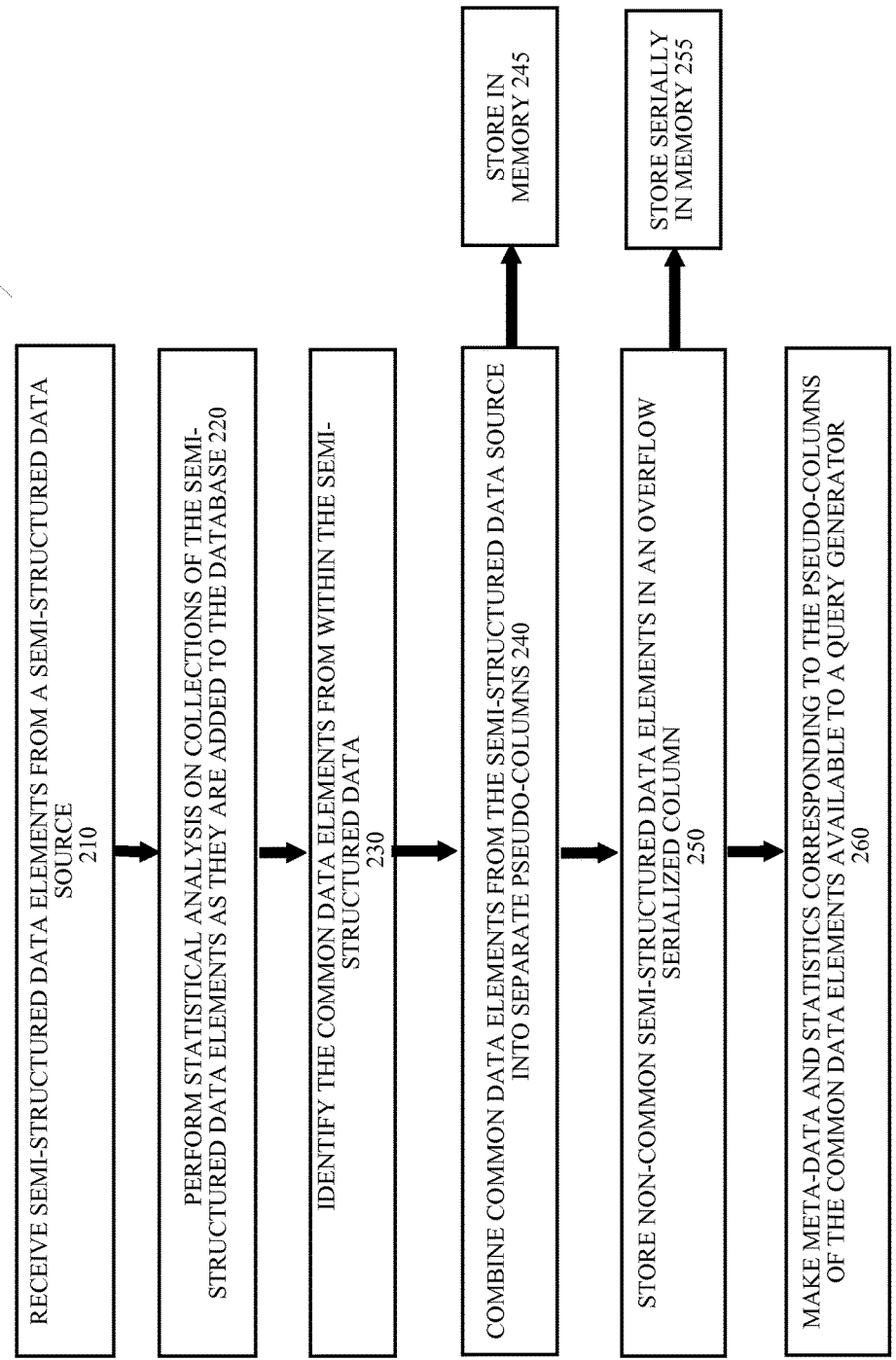
FIG. 2 is a process flow diagram depicting an implementation of the methods disclosed herein.

FIG. 2 illustrates a flow diagram of a method 200 for handling semi structured data. As can be seen in the figure, at 210 semi structured data elements are received from a semi structured data source, or a plurality of semi structure data sources. This is achieved by performing statistical analysis of the collections of semi-structured data records as they are added to the database at 220 and identifying common data elements at 230. The system performing the instructions of method 200 may further combine storage of common data elements from the semi-structured data in separate pseudo-columns at 240, while the less common data elements are stored in "overflow" serialized representation at 250. These elements are extracted from the semi-structured data, and stored separately in columnar format invisibly to users at 245, while at 250 the rest of the semi-structured data is stored in a serialized format in a main column at 255. It will be appreciated that the metadata and statistics (such as min and max values, number of distinct values, etc.) of these pseudo-columns may be then made available to the query generator at 260. Note that separate collections (i.e. parts of the table stored in the separate files) may have different subsets of data elements extracted.

In an implementation, when extracting data, if a value of a common data element is needed, it may be obtained directly from the corresponding pseudo-column, using efficient columnar access.

In an implementation, a bloom filter may be employed to control resource use. Bloom filters may use identifiers of data elements within semi-structured data to filter data as it is ingested and consumed by the system and processes.

For a user, this method may be indistinguishable from storing serialized records, and imposes no constraints on structure of individual data records. However, because most common data elements are stored in the same way as conventional relational data, access to them may be provided and may not require reading and extraction of the entire semi-structured records, thus gaining the speed advantages of conventional relational databases.

Because the different collections of semi-structured records (from the same table) may have different sets of data elements extracted, the query generator and the pruning should be able to work with partially available metadata (i.e. parts of the table may have metadata and statistics available for a particular data element, while other parts may lack it).

An advantage over the prior art is the ability provided by the method for using a hybrid data storage representation (as both serialized storage of less common elements and columnar storage of common elements). This allows users to achieve both flexibility and ability to store arbitrary semi-structured data of systems using serialized representation and high performance of data queries provided by conventional relational data bases.

Additionally, semi-structured data may represent entire files, partial files, collections of files, and partial collections of files. It should be noted that a semi-structured data element may be a file or a portion of a file. In an implementation, metadata may be used to define data and to assist in its organization and use.

It will be appreciated by those in the art that any data processing platform could use this approach to handling semi-structured data. It does not need to be limited to a DBMS system running SQL.

Figure 3:
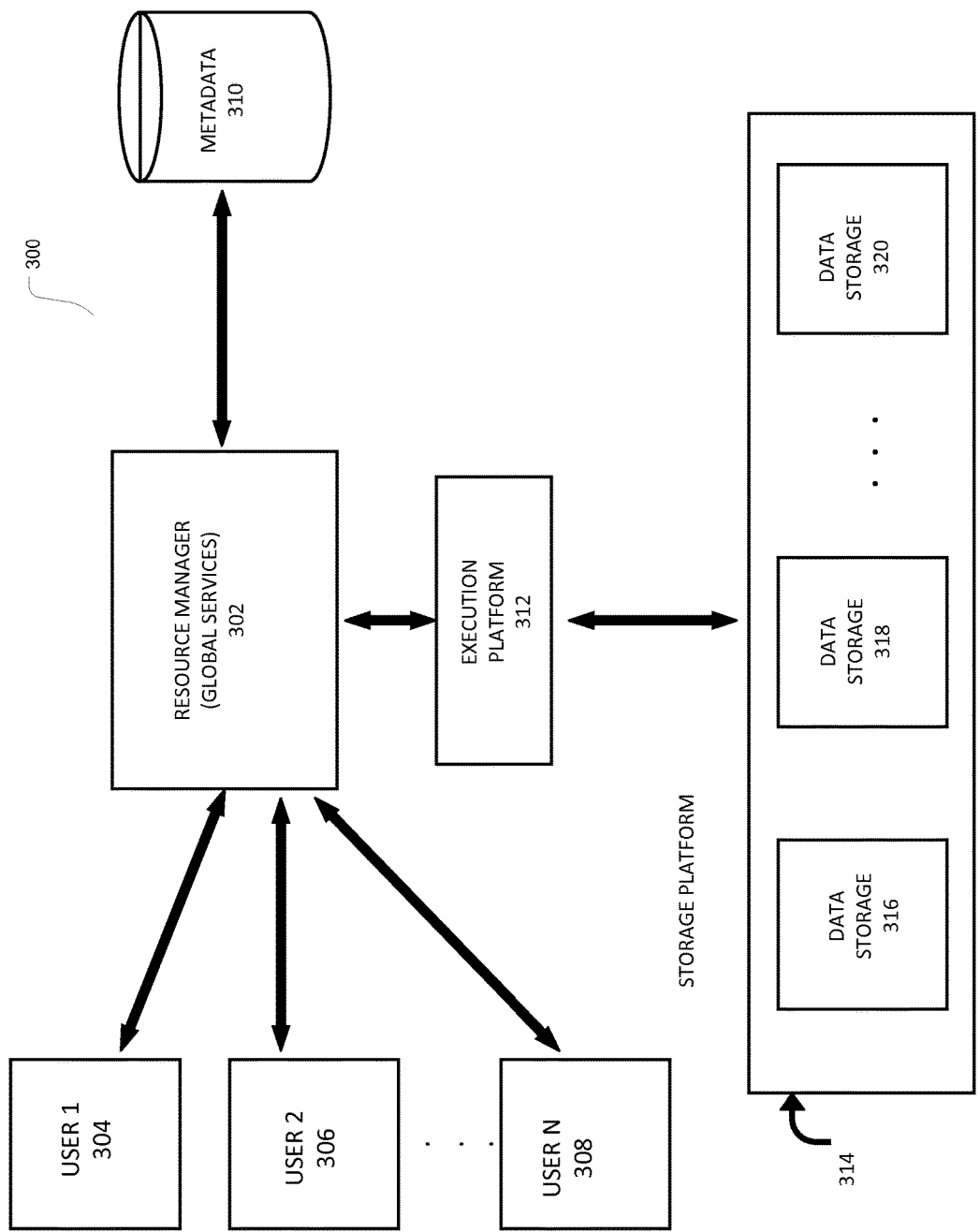
FIG. 3 illustrates a block diagram depicting an embodiment of an operating environment in accordance with the teachings of the disclosure.

Illustrated in FIG. 3 is a computer system for running the methods disclosed herein. As shown in FIG. 3, a resource manager 302 is coupled to multiple users 304, 306, and 308. In particular implementations, resource manager 302 can support any number of users desiring access to data processing platform 300. Users 304-308 may include, for example, end users providing data storage and retrieval requests, system administrators managing the systems and methods described herein, software applications that interact with a database, and other components/devices that interact with resource manager 302. Resource manager 302 provides various services and functions that support the operation of all systems and components within data processing platform 300. Resource manager 302 is also coupled to metadata 310, which is associated with the entirety of data stored throughout data processing platform 300. Because the resource manager is coupled with the metadata corresponding to sets of files, the metadata may be used for generating user queries. In some embodiments, metadata 310 includes a summary of data stored in remote data storage systems as well as data available from a local cache. Additionally, metadata 310 may include information regarding how data is organized in the remote data storage systems and the local caches. Metadata 310 allows systems and services to determine whether a piece of data needs to be processed without loading or accessing the actual data from a storage device.

Resource manager 302 is further coupled to an execution platform 312, which provides multiple computing resources that execute various data storage and data retrieval tasks, as discussed in greater detail below. Execution platform 312 is coupled to multiple data storage devices 316, 318, and 320 that are part of a storage platform 314. Although three data storage devices 316, 318, and 320 are shown in FIG. 3, execution platform 312 is capable of communicating with any number of data storage devices. In some embodiments, data storage devices 316, 318, and 320 are cloud-based storage devices located in one or more geographic locations. For example, data storage devices 316, 318, and 320 may be part of a public cloud infrastructure or a private cloud infrastructure. Data storage devices 316, 318, and 320 may be hard disk drives (HDDs), solid state drives (SSDs), storage clusters or any other data storage technology. Additionally, storage platform 314 may include distributed file systems (such as Hadoop Distributed File Systems (HDFS)), object storage systems, and the like.

In particular embodiments, the communication links between resource manager 302 and users 304-308, metadata 310, and execution platform 312 are implemented via one or more data communication networks. Similarly, the communication links between execution platform 312 and data storage devices 316-320 in storage platform 314 are implemented via one or more data communication networks. These data communication networks may utilize any communication protocol and any type of communication medium. In some embodiments, the data communication networks are a combination of two or more data communication networks (or sub-networks) coupled to one another. In alternate embodiments, these communication links are implemented using any type of communication medium and any communication protocol.

As shown in FIG. 3, data storage devices 316, 318, and 320 are decoupled from the computing resources associated with execution platform 312. This architecture supports dynamic changes to data processing platform 300 based on the changing data storage/retrieval needs as well as the changing needs of the users and systems accessing data processing platform 300. The support of dynamic changes allows data processing platform 300 to scale quickly in response to changing demands on the systems and components within data processing platform 300. The decoupling of the computing resources from the data storage devices supports the storage of large amounts of data without requiring a corresponding large amount of computing resources. Similarly, this decoupling of resources supports a significant increase in the computing resources utilized at a particular time without requiring a corresponding increase in the available data storage resources.

Resource manager 302, metadata 310, execution platform 312, and storage platform 314 are shown in FIG. 3 as individual components. However, each of resource manager 302, metadata 310, execution platform 312, and storage platform 314 may be implemented as a distributed system (e.g., distributed across multiple systems/platforms at multiple geographic locations). Additionally, each of resource manager 302, metadata 310, execution platform 312, and storage platform 314 can be scaled up or down (independently of one another) depending on changes to the requests received from users 304-308 and the changing needs of data processing platform 300. Thus, in the described embodiments, data processing platform 300 is dynamic and supports regular changes to meet the current data processing needs.

Figure 4:
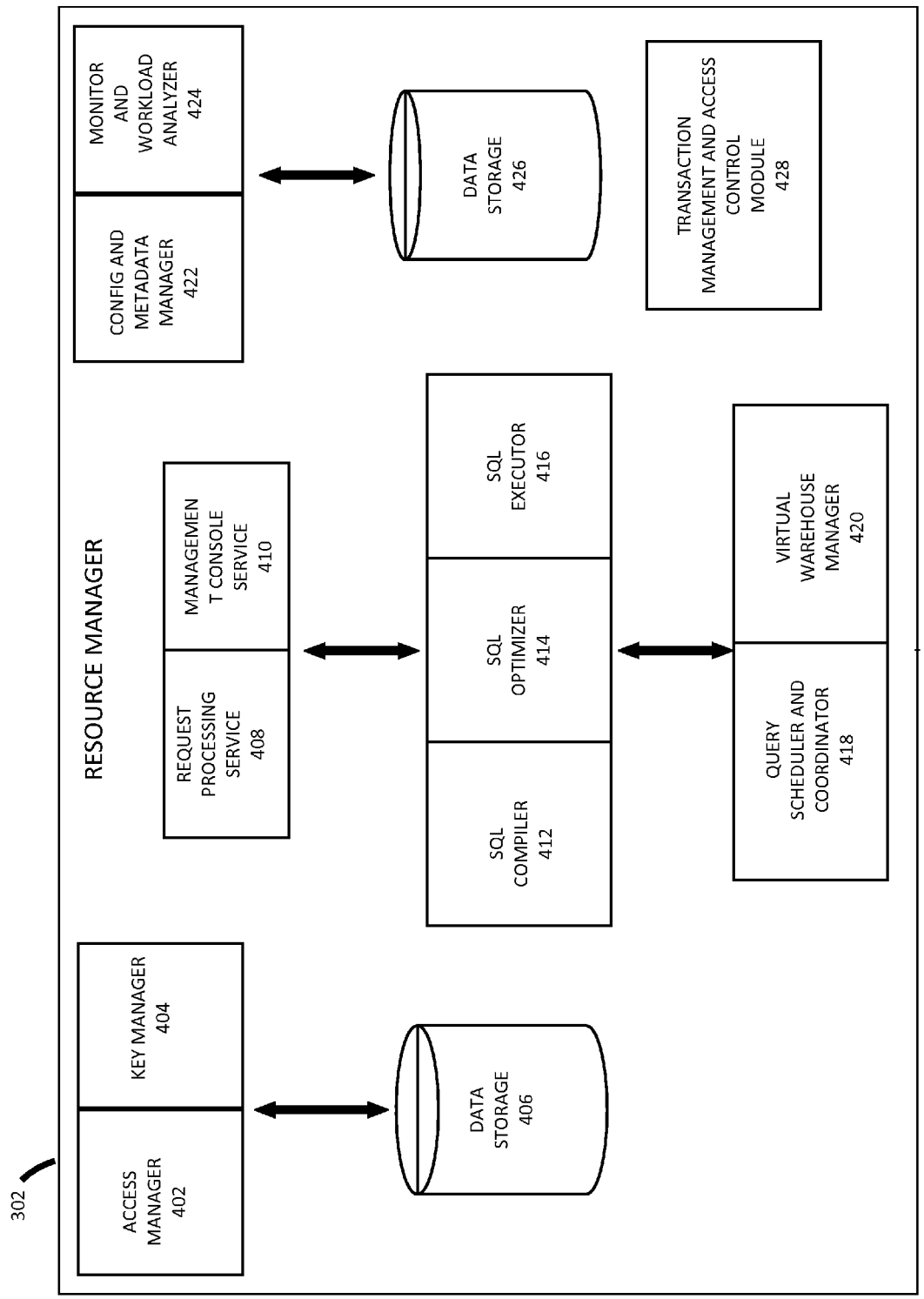
FIG. 4 illustrates a block diagram depicting an example of an implementation of a resource manager in accordance with the teachings of the disclosure.

FIG. 4 is a block diagram depicting an embodiment of resource manager 302. As shown in FIG. 3, resource manager 302 includes an access manager 402 and a key manager 404 coupled to a data storage device 406. Access manager 402 handles authentication and authorization tasks for the systems described herein. Key manager 404 manages storage and authentication of keys used during authentication and authorization tasks. A request processing service 408 manages received data storage requests and data retrieval requests. A management console service 410 supports access to various systems and processes by administrators and other system managers.

Resource manager 302 also includes an SQL compiler 412, an SQL optimizer 414 and an SQL executor 410. SQL compiler 412 parses SQL queries and generates the execution code for the queries. SQL optimizer 414 determines the best method to execute queries based on the data that needs to be processed. SQL executor 416 executes the query code for queries received by resource manager 302. A query scheduler and coordinator 418 sends received queries to the appropriate services or systems for compilation, optimization, and dispatch to an execution platform. A virtual warehouse manager 420 manages the operation of multiple virtual warehouses implemented in an execution platform.

Additionally, resource manager 302 includes a configuration and metadata manager 422, which manages the information related to the data stored in the remote data storage devices and in the local caches. A monitor and workload analyzer 424 oversees the processes performed by resource manager 302 and manages the distribution of tasks (e.g., workload) across the virtual warehouses and execution nodes in the execution platform. Configuration and metadata manager 422 and monitor and workload analyzer 424 are coupled to a data storage device 426.

Resource manager 302 also includes a transaction management and access control module 428, which manages the various tasks and other activities associated with the processing of data storage requests and data access requests. For example, transaction management and access control module 428 provides consistent and synchronized access to data by multiple users or systems. Since multiple users/systems may access the same data simultaneously, changes to the data must be synchronized to ensure that each user/system is working with the current version of the data. Transaction management and access control module 428 provides control of various data processing activities at a single, centralized location in resource manager 302.

Figure 5:
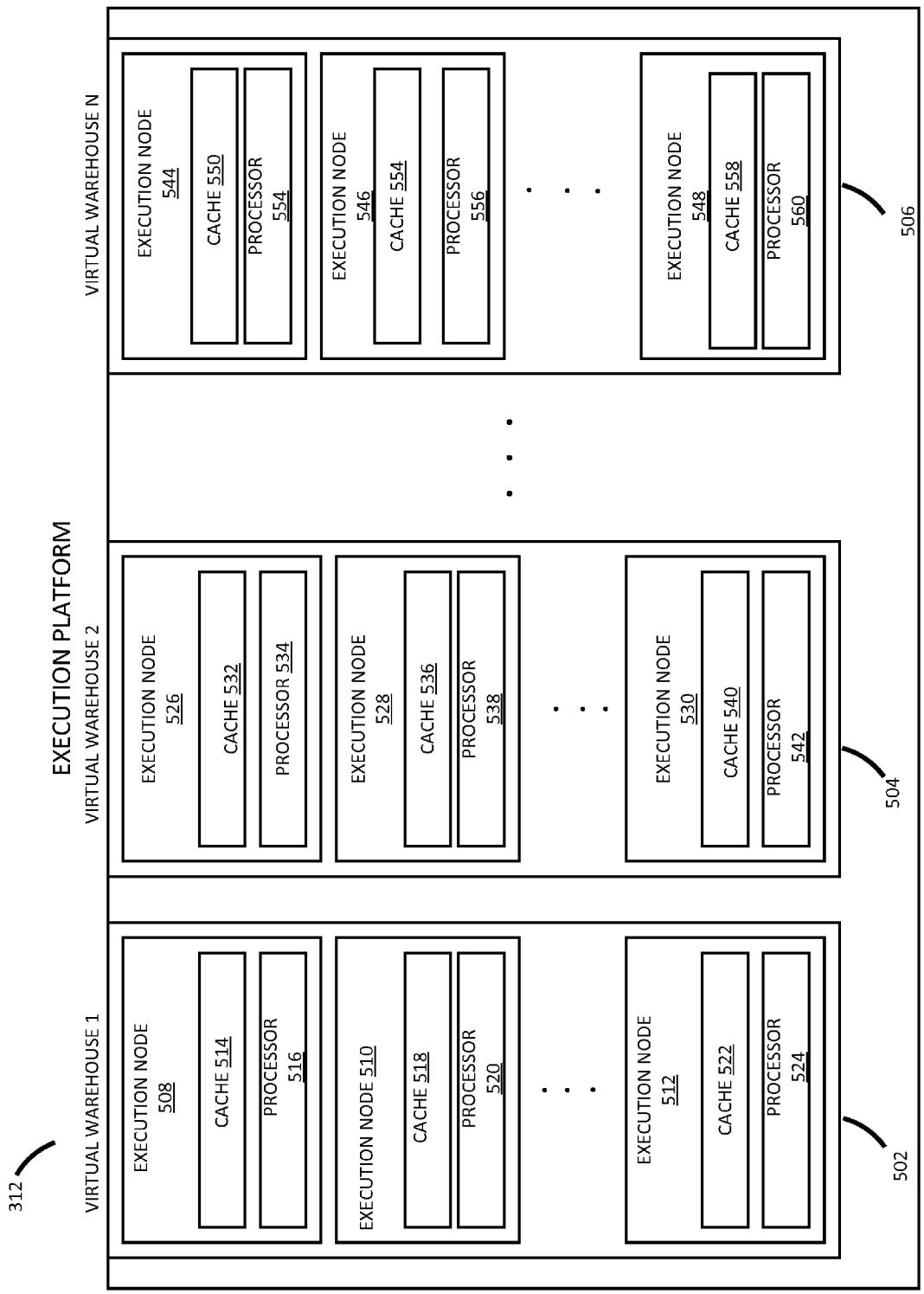
FIG. 5 illustrates a block diagram depicting an example of an implementation of a execution platform in accordance with the teachings of the disclosure.

FIG. 5 is a block diagram depicting an embodiment of an execution platform. As shown in FIG. 5, execution platform 512 includes multiple virtual warehouses 502, 504, and 506. Each virtual warehouse includes multiple execution nodes that each include a cache and a processor. Although each virtual warehouse 502-506 shown in FIG. 5 includes three execution nodes, a particular virtual warehouse may include any number of execution nodes. Further, the number of execution nodes in a virtual warehouse is dynamic, such that new execution nodes are created when additional demand is present, and existing execution nodes are deleted when they are no longer necessary.

Each virtual warehouse 502-506 is capable of accessing any of the data storage devices 316-320 shown in FIG. 3. Thus, virtual warehouses 502-506 are not necessarily assigned to a specific data storage device 316-320 and, instead, can access data from any of the data storage devices 316-320. Similarly, each of the execution nodes shown in FIG. 5 can access data from any of the data storage devices 316-320. In some embodiments, a particular virtual warehouse or a particular execution node may be temporarily assigned to a specific data storage device, but the virtual warehouse or execution node may later access data from any other data storage device.

In the example of FIG. 5, virtual warehouse 502 includes three execution nodes 508, 510, and 512. Execution node 508 includes a cache 514 and a processor 516. Execution node 510 includes a cache 518 and a processor 520. Execution node 512 includes a cache 522 and a processor 524. Each execution node 508-512 is associated with processing one or more data storage and/or data retrieval tasks. For example, a particular virtual warehouse may handle data storage and data retrieval tasks associated with a particular user or customer. In other implementations, a particular virtual warehouse may handle data storage and data retrieval tasks associated with a particular data storage system or a particular category of data.

Similar to virtual warehouse 502 discussed above, virtual warehouse 504 includes three execution nodes 526, 528, and 530. Execution node 526 includes a cache 532 and a processor 534. Execution node 528 includes a cache 536 and a processor 538. Execution node 530 includes a cache 540 and a processor 542. Additionally, virtual warehouse 506 includes three execution nodes 544, 546, and 548. Execution node 544 includes a cache 550 and a processor 552. Execution node 546 includes a cache 554 and a processor 556. Execution node 548 includes a cache 558 and a processor 560.

Although the execution nodes shown in FIG. 5 each include one cache and one processor, alternate embodiments may include execution nodes containing any number of processors and any number of caches. Additionally, the caches may vary in size among the different execution nodes. The caches shown in FIG. 5 store, in the local execution node, data that was retrieved from one or more data storage devices in a storage platform 314 (FIG. 3). Thus, the caches reduce or eliminate the bottleneck problems occurring in platforms that consistently retrieve data from remote storage systems. Instead of repeatedly accessing data from the remote storage devices, the systems and methods described herein access data from the caches in the execution nodes which is significantly faster and avoids the bottleneck problem discussed above. In some embodiments, the caches are implemented using high-speed memory devices that provide fast access to the cached data. Each cache can store data from any of the storage devices in storage platform 314.

Further, the cache resources and computing resources may vary between different execution nodes. For example, one execution node may contain significant computing resources and minimal cache resources, making the execution node useful for tasks that require significant computing resources. Another execution node may contain significant cache resources and minimal computing resources, making this execution node useful for tasks that require caching of large amounts of data. In some embodiments, the cache resources and computing resources associated with a particular execution node are determined when the execution node is created, based on the expected tasks to be performed by the execution node.

Additionally, the cache resources and computing resources associated with a particular execution node may change over time based on changing tasks performed by the execution node. For example, a particular execution node may be assigned more processing resources if the tasks performed by the execution node become more processor intensive. Similarly, an execution node may be assigned more cache resources if the tasks performed by the execution node require a larger cache capacity.

Although virtual warehouses 502-506 are associated with the same execution platform 312 of FIG. 3, the virtual warehouses may be implemented using multiple computing systems at multiple geographic locations. For example, virtual warehouse 502 can be implemented by a computing system at a first geographic location, while virtual warehouses 504 and 506 are implemented by another computing system at a second geographic location. In some embodiments, these different computing systems are cloud-based computing systems maintained by one or more different entities.

Additionally, each virtual warehouse is shown in FIG. 5 as having multiple execution nodes. The multiple execution nodes associated with each virtual warehouse may be implemented using multiple computing systems at multiple geographic locations. For example, a particular instance of virtual warehouse 502 implements execution nodes 508 and 510 on one computing platform at a particular geographic location, and implements execution node 512 at a different computing platform at another geographic location. Selecting particular computing systems to implement an execution node may depend on various factors, such as the level of resources needed for a particular execution node (e.g., processing resource requirements and cache requirements), the resources available at particular computing systems, communication capabilities of networks within a geographic location or between geographic locations, and which computing systems are already implementing other execution nodes in the virtual warehouse. Execution platform 312 is also fault tolerant. For example, if one virtual warehouse fails, that virtual warehouse is quickly replaced with a different virtual warehouse at a different geographic location.

A particular execution platform 312 may include any number of virtual warehouses 502-506. Additionally, the number of virtual warehouses in a particular execution platform is dynamic, such that new virtual warehouses are created when additional processing and/or caching resources are needed. Similarly, existing virtual warehouses may be deleted when the resources associated with the virtual warehouse are no longer necessary.

Figure 6:
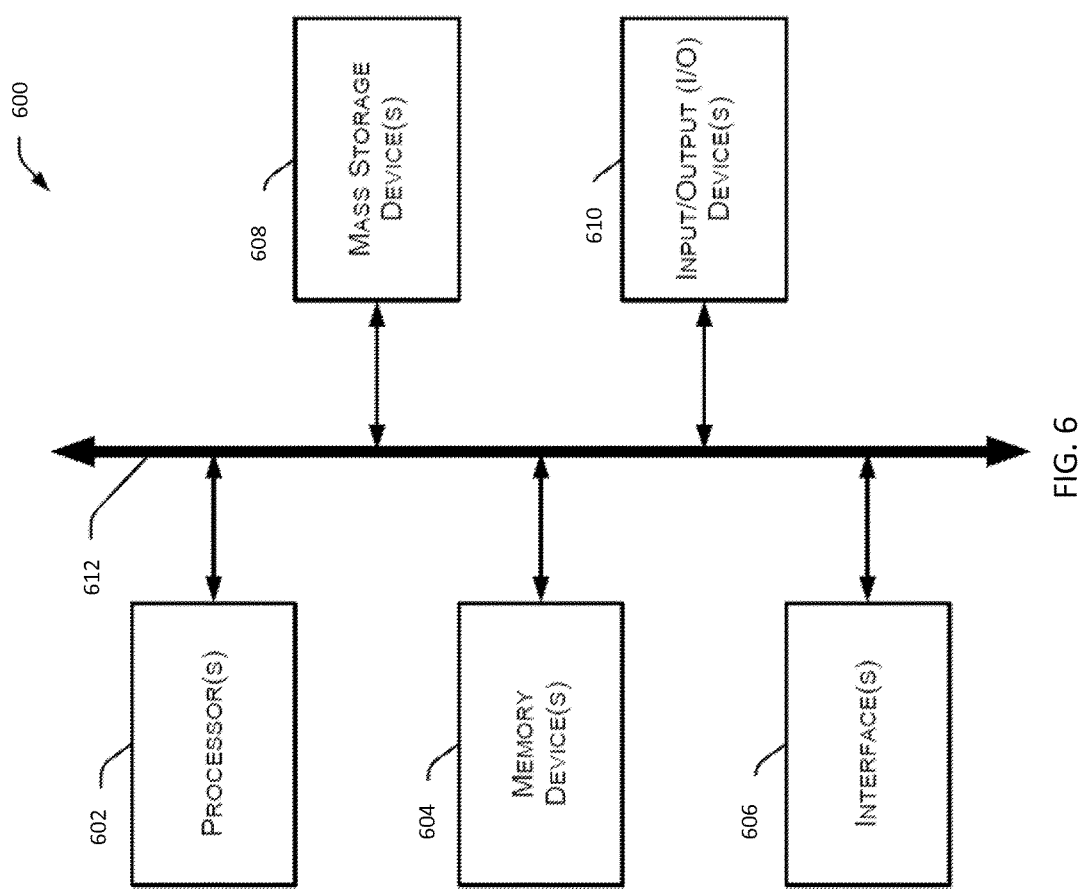
FIG. 6 illustrates a block diagram depicting an example computing device in accordance with the teachings of the disclosure.

FIG. 6 is a block diagram depicting an example computing device 600. In some embodiments, computing device 600 is used to implement one or more of the systems and components discussed herein. For example, computing device 600 may allow a user or administrator to access resource manager 302. Further, computing device 600 may interact with any of the systems and components described herein. Accordingly, computing device 600 may be used to perform various procedures and tasks, such as those discussed herein. Computing device 600 can function as a server, a client or any other computing entity. Computing device 600 can be any of a wide variety of computing devices, such as a desktop computer, a notebook computer, a server computer, a handheld computer, a tablet, and the like.

Computing device 600 includes one or more processor(s) 602, one or more memory device(s) 604, one or more interface(s) 606, one or more mass storage device(s) 608, and one or more Input/Output (I/O) device(s) 610, all of which are coupled to a bus 612. Processor(s) 602 include one or more processors or controllers that execute instructions stored in memory device(s) 604 and/or mass storage device(s) 608. Processor(s) 602 may also include various types of computer-readable media, such as cache memory.

Memory device(s) 604 include various computer-readable media, such as volatile memory (e.g., random access memory (RAM)) and/or nonvolatile memory (e.g., read-only memory (ROM)). Memory device(s) 604 may also include rewritable ROM, such as Flash memory.

Mass storage device(s) 608 include various computer readable media, such as magnetic tapes, magnetic disks, optical disks, solid state memory (e.g., Flash memory), and so forth. Various drives may also be included in mass storage device(s) 608 to enable reading from and/or writing to the various computer readable media. Mass storage device(s) 608 include removable media and/or non-removable media.

I/O device(s) 610 include various devices that allow data and/or other information to be input to or retrieved from computing device 600. Example I/O device(s) 610 include cursor control devices, keyboards, keypads, microphones, monitors or other display devices, speakers, printers, network interface cards, modems, lenses, CCDs or other image capture devices, and the like.

Interface(s) 606 include various interfaces that allow computing device 600 to interact with other systems, devices, or computing environments. Example interface(s) 606 include any number of different network interfaces, such as interfaces to local area networks (LANs), wide area networks (WANs), wireless networks, and the Internet.

Bus 612 allows processor(s) 602, memory device(s) 604, interface(s) 606, mass storage device(s) 608, and I/O device(s) 610 to communicate with one another, as well as other devices or components coupled to bus 612. Bus 612 represents one or more of several types of bus structures, such as a system bus, PCI bus, IEEE 1394 bus, USB bus, and so forth.

For purposes of illustration, programs and other executable program components are shown herein as discrete blocks, although it is understood that such programs and components may reside at various times in different storage components of computing device 600, and are executed by processor(s) 602. Alternatively, the systems and procedures described herein can be implemented in hardware, or a combination of hardware, software, and/or firmware. For example, one or more application specific integrated circuits (ASICs) can be programmed to carry out one or more of the systems and procedures described herein.

Although the present disclosure is described in terms of certain preferred embodiments, other embodiments will be apparent to those of ordinary skill in the art, given the benefit of this disclosure, including embodiments that do not provide all of the benefits and features set forth herein, which are also within the scope of this disclosure. It is to be understood that other embodiments may be utilized, without departing from the scope of the present disclosure.

The invention claimed is:

1. A method for managing semi-structured data comprising:
    receiving semi-structured data elements from a data source that is connected over a computer network;
    performing statistical analysis on collections of the semi-structured data elements as they are added to the database via a computer processor, wherein separate collections comprising portions of the semi-structured data are stored in separate files having different subsets of the semi-structured data elements that have been extracted;
    identifying common data elements from within the semi-structured data;
    combining common data elements from the data source into separate pseudo-columns;
    storing non-common semi-structured data elements in an overflow serialized column in computer memory; and
    deriving metadata corresponding to the pseudo-columns of the common data elements from the statistical analysis.

2. The method of claim 1, wherein the common data elements are extracted from the semi-structured data and stored separately in a columnar format.

3. The method of claim 2, wherein the pseudo-columns are not made visible to users.

4. The method of claim 1, further comprising storing the non-common semi-structured data in a serialized format in a main column.

5. The method of claim 1, further comprising filtering with a bloom filter comprising identifiers of data elements contained within the separate collections.

6. The method of claim 1, wherein metadata for each pseudo column comprises at least one of:
    minimum and maximum values within a corresponding pseudo column,
    a number representing the number of times distinct values appear in the column.

7. The method of claim 1, further comprising extracting data elements from overflow serialized data if the data element requested is not in a pseudo-column.

8. The method of claim 1, further comprising reconstructing semi-structured data to an original form by extracting data elements from pseudo-columns and from the overflow serialized data.

9. The method of claim 1, further comprising updating the metadata corresponding to the pseudo-columns as additional semi-structured data is received.

10. A system for aggregating semi-structured data comprising:
    one or more processors;
    memory operably connected to the one or more processors; and
    the memory storing one or more modules programmed to:
        receive semi-structured data elements from a data source;
        perform statistical analysis on collections of the semi-structured data elements as they are added to the database, wherein separate collections comprising portions of the semi-structured data are stored in separate files having different subsets of the semi-structured data elements that have been extracted;
        identify common data elements from within the semi-structured data and combine the common data elements from the data source into separate pseudo-columns;
        store non-common semi-structured data elements in an overflow serialized column; and
        derive metadata corresponding to the pseudo-columns of the common data elements from the statistical analysis.

11. The system of claim 10, wherein the combining the common data elements from the data source into separate pseudo-columns comprises extracting common data elements from the semi-structured data and storing the common data elements separately in a columnar format.

12. The system of claim 10, wherein the columnar format is invisible to users.

13. The system of claim 10, wherein metadata for each pseudo-column comprises at least one of:
    minimum and maximum values within a corresponding pseudo column, and a number representing the number of times distinct values appear in the column.

14. An apparatus for aggregating semi-structured data comprising:
  one or more processors;
  memory operably connected to the one or more processors; and
  the memory storing:
    a receiving module configured to receive semi-structured data elements from a data source;
    a statistical module configured to perform statistical analysis on collections of the semi-structured data elements as they are added to the database, wherein separate collections comprising portions of the semi-structured data are stored in separate files having different subsets of the semi-structured data elements that have been extracted;
    an aggregation means for identifying common data elements from within the semi-structured data and combining the common data elements from the data source into separate pseudo-columns;
    the aggregation means further for serializing and storing non-common semi-structured data elements in an overflow serialized column; and
    the aggregation means further for deriving metadata corresponding to the pseudo-columns of the common data elements from the statistical analysis.

15. The apparatus of claim 14, wherein the combining the common data elements from the data source into separate pseudo-columns comprises extracting common data elements from the semi-structured data and storing the common data elements separately in a columnar format.

16. The apparatus of claim 14, wherein the columnar format is invisible to users.

17. The apparatus of claim 14, wherein metadata for each pseudo column comprises at least one of:
  minimum and maximum values within a corresponding pseudo column, and
  a number representing the number of times distinct values appear in the column.

18. The apparatus of claim 14, wherein the aggregation means is further for updating the metadata corresponding to the pseudo-columns as additional semi-structured data is received.

* * * * *